US010105862B1

(12) United States Patent
Koch et al.

(10) Patent No.: US 10,105,862 B1
(45) Date of Patent: Oct. 23, 2018

(54) FENESTRATED GRAFT PRESS CUTTING DIE ASSEMBLY

(71) Applicant: BioCut, LLC, Milwaukee, WI (US)

(72) Inventors: Jared Koch, Milwaukee, WI (US); John Reimer, Wauwatosa, WI (US); Eric Schmitt, Sussex, WI (US)

( * ) Notice: Subject to any disclaimer, the term of this patent is extended or adjusted under 35 U.S.C. 154(b) by 105 days.

(21) Appl. No.: 15/475,530

(22) Filed: Mar. 31, 2017

(51) Int. Cl.
*B26D 1/06* (2006.01)
*A61F 2/10* (2006.01)

(52) U.S. Cl.
CPC ............. *B26D 1/065* (2013.01); *A61F 2/105* (2013.01)

(58) Field of Classification Search
CPC .................. B26D 1/065; A61F 2/105
See application file for complete search history.

(56) References Cited

U.S. PATENT DOCUMENTS

| | | | |
|---|---|---|---|
| 2,313,801 A | 3/1943 | Carll | |
| 2,495,221 A | 1/1950 | Berlin | |
| 2,703,023 A | 3/1955 | Sarno | |
| 2,821,871 A | 2/1958 | Sarno | |
| 2,939,347 A | 6/1960 | Tobey | |
| 3,020,785 A | 2/1962 | Leavesley et al. | |
| 3,048,069 A | 8/1962 | Berlin et al. | |
| 3,120,601 A | 2/1964 | Berlin et al. | |
| 3,152,492 A * | 10/1964 | Whitecotton | B21D 37/205 76/107.8 |
| 3,182,530 A * | 5/1965 | Scott | B26F 1/00 493/338 |
| 3,194,090 A | 7/1965 | Becker | |
| 3,228,263 A | 1/1966 | Bien | |
| 3,292,461 A | 12/1966 | Bien | |
| 3,383,969 A | 5/1968 | Saunders | |
| 3,396,620 A * | 8/1968 | Raphael | B21D 37/205 76/107.8 |
| 3,587,377 A * | 6/1971 | Olson | B26D 7/10 219/601 |
| 3,737,365 A | 6/1973 | Smith | |
| 3,786,732 A * | 1/1974 | Forbes, Jr. | B26F 1/44 493/354 |
| 3,835,746 A | 9/1974 | Young, Jr. et al. | |
| 3,941,038 A * | 3/1976 | Bishop | B26D 7/2614 493/371 |
| 4,052,886 A * | 10/1977 | Buick | B26F 1/44 493/468 |
| 4,226,143 A | 10/1980 | Whitecotton et al. | |
| 4,249,432 A * | 2/1981 | Graboyes | B23P 15/406 76/107.8 |
| 4,598,206 A * | 7/1986 | Nelson | G01J 5/522 250/494.1 |

(Continued)

*Primary Examiner* — Sean Michalski

(57) ABSTRACT

An assembly and method of forming a press cutting die assembly that is configured to perforate a tissue graft blank during cutting of the blank from a bulk graft material. The press cutting die assembly includes a frame, a perimeter blade, and a plurality of fenestration blades that extend between respective portions of the perimeter blade. In a preferred embodiment, the plurality of fenestration blades are provided in at least two groups to form a repeating pattern of preferably uniformly spaced perforations within the perimeter of the blank. Such a press cutting die assembly is particularly applicable for cutting biologically compatible materials having a desired shape and uniform fenestration pattern from a bulk source of the biologically compatible material.

20 Claims, 8 Drawing Sheets

(56) References Cited

U.S. PATENT DOCUMENTS

| | | | |
|---|---|---|---|
| 5,140,872 A | | 8/1992 | Holliday et al. |
| 5,211,084 A | * | 5/1993 | Holliday .............. B26F 1/44 |
| | | | 219/121.67 |
| 5,943,935 A | * | 8/1999 | Brayton .............. B26F 1/44 |
| | | | 493/354 |
| 6,189,414 B1 | * | 2/2001 | Yoshizawa .......... B23P 15/406 |
| | | | 76/107.8 |
| 6,626,965 B2 | | 9/2003 | Workman et al. |
| 6,889,588 B1 | | 5/2005 | Jenkins |
| 2005/0197699 A1 | * | 9/2005 | Jacobs ................ A61F 2/0811 |
| | | | 623/13.14 |
| 2007/0183974 A1 | * | 8/2007 | Pearlman ............ A61B 17/322 |
| | | | 424/9.1 |
| 2011/0251602 A1 | * | 10/2011 | Anderson ........ A61B 17/32093 |
| | | | 606/13 |
| 2013/0085570 A1 | * | 4/2013 | Rose .................... B26F 1/24 |
| | | | 623/15.12 |
| 2015/0059544 A1 | * | 3/2015 | Ohnishi .............. B26D 1/0006 |
| | | | 83/168 |
| 2015/0140058 A1 | * | 5/2015 | Tumey ................ A61L 27/56 |
| | | | 424/423 |
| 2015/0151531 A1 | * | 6/2015 | Ohno .................. B32B 43/006 |
| | | | 156/755 |
| 2015/0327699 A1 | * | 11/2015 | Habib ................ B65D 81/2015 |
| | | | 206/234 |
| 2016/0221206 A1 | * | 8/2016 | Jeske .................. B26F 1/40 |
| 2017/0165859 A1 | * | 6/2017 | Kropf .................. B26D 1/065 |

* cited by examiner

FENESTRATED GRAFT PRESS CUTTING DIE ASSEMBLY

FIELD OF THE INVENTION

The present invention relates generally to press cutting dies and, more particularly, to a press cutting die assembly that is constructed of medical grade materials and which fenestrates a graft tissue blank during cutting of the tissue graft blanks from bulk graft material.

BACKGROUND OF THE INVENTION

As commonly understood, skin or other tissue grafting processes commonly involve the transplanting of a section of tissue to an injury of other anatomical abnormality associated with damage to or a loss of tissue. Some grafting processes involve the transplantation of a section of tissue from one area of a patient to another area of a patient. Other grafting processes; such, as allogeneic grafts (where donors and recipients are the same species), xenogeneic grafts (where donors and recipients are different species, such as porcine grafts), and prosthetic grafts (which include synthetic graft materials); can commonly be effectuated by cutting a graft from a sheet of graft material and subsequently applying the cut graft to the intended graft location. Various considerations must be addressed when forming grafts in such a manner.

One consideration to graft preparation relates to providing a sanitary condition associated with the entire process of forming each discrete tissue graft. Failure to properly attend to the sanitation of the process can result in contamination between the various devices associated with the cutting process, the blank materials, as well as already cut graft materials. Still further, inadequate attention to sanitary conditions can result in cross-contamination between already cut grafts, subsequent blank materials, and even subsequent material lots. Accordingly, devices associated with such tissue cutting processes must commonly be disposable and/or constructed to withstand periodic exposure to a suitable sanitation process to mitigate contamination between respective grafts.

Whether provided in a disposable or reusable configuration, another consideration that must be addressed during die formation is the suitability of the materials associated with forming or defining the die as being suitable for exposure to materials or tissues which are ultimately intended to be associated with and supported by a host body. That is, the die assembly and generation of the grafts preferably does not transfer materials that are ill-suited and/or dangerous for biological applications to the grafts.

Another consideration of the press cut generation of tissue grafts relates to providing a graft product that can satisfy generally uniform or repeatable size parameters. In order to press cut graft materials, a cutting edge defined by a press die must be maintained in a generally planar arrangement such, that the cutting edge can pass through the graft material in a substantially orthogonal direction relative to the exposed surface plane of the material to generate grafts that are of substantially the same size and which maintain a robust graft edge for subsequent cooperation adjacent tissue of an underlying patient. Movement of the cutting edge relative to an underlying blade support or deviation of the blade during die formation and/or sterilization process can result in a die configuration that is susceptible to incomplete cut operations or undesirable cut profiles. Such shortcomings can detract from a repeatable generation of a uniform graft product and/or decrease the efficiency with which grafts can be created.

Still further considerations associated with graft production relate to improving the acceptance or integration of the graft during healing. Commonly, graft tissue blanks are prepared, during or immediately prior to use, by meshing, also called fenestration. During fenestration, small perforations, slits, or cuts are formed in the donor tissue. These fenestrations allow the donor graft to be stretched thereby increasing the surface area of the donor graft and reducing the amount of graft material needed to reconstruct damaged dermis. In autograft processes, such considerations reduces the trauma and scarring associated with the donor area and allows the donor area to heal more quickly than it would if more graft tissue were harvested.

Fenestration of graft material also improves healing of the wound area. The perforations, and openings associated therewith due to stretching of the donor graft material, increases the amount of graft perimeter available for capillary pass-through and connection with other vessels. The openings associated with the fenestrations also allows fluids produced by the wound during healing to drain thereby mitigating capture of the fluid which may lead to infection between the graft and the wound.

Donor graft material is commonly fenestrated manually through the use of either a scalpel or by passing the donor graft tissue through a mechanical mesher. Such approaches have various drawbacks. Manually meshing the graft tissue with a scalpel can be tedious and requires the time and skill of highly qualified technicians. Even with the most skilled technicians, such processing often produces a less than uniform fenestration pattern which can result in undesired tearing and/or non-uniform presentation of the openings associated with the fenestrations when the graft tissue is stretched during use. Although mechanical meshers tend to mitigate some of the concerns associated with uniform fenestration production, use of such machines present their own complications associated with production of the desired fenestrated graft tissue.

Mechanical meshes commonly rely on using opposing rollers that flatten and perforate the graft tissue as it is passed therethrough. Such treatment of the donor graft tissue is unduly aggressive and can result in blemishes such as pock marks or the like in healed tissue. Such blemishes, depending on the severity and patient location, commonly require additional cosmetic surgery to resolve. Still further, donor graft tissue can commonly become torn or entangled when passed through such mechanical meshes. The severity of the damage to the tissue can render the graft tissue unusable for its intended purpose and effectively wasting the same. Such considerations are particularly problematic during autograft processes. Still further, during mechanical meshing, small particles of biological material may separate from the graft and remain adhered to the mesher thereby complicating the ability to maintain the desired level of sanitation associated with the same. Still further, both manual fenestration and utilization of mechanical meshers require clean room levels of sterilization yet further increasing costs associated with production of the same.

Accordingly, it would be desirable to have an assembly and method for generating fenestrated graft tissue blanks in a more uniform, sanitary, and conveniently implemental manner. The present invention discloses a press cut die assembly and method of forming a die assembly for generating fenestrated graft tissue blanks.

BRIEF DESCRIPTION OF THE INVENTION

The present invention provides a press cutting die assembly and method of forming a press cutting die assembly that overcomes one or more of the drawbacks mentioned above. One aspect of the application discloses a press cutting die assembly that is configured to perforate a blank during cutting of the blank from a bulk material. The press cutting die assembly includes a frame, a perimeter blade assembly, and a plurality of graft field perforation blades that extend between respective portions of the perimeter blade assembly. In a preferred aspect, the plurality of perforation blades are provided in at least two groups to form a repeating pattern of preferably uniformly spaced perforations within the perimeter of the graft blank.

Another aspect of the application discloses a press cutting die assembly that includes a frame that is configured to support a blade stack. The blade stack includes a perimeter blade assembly that is configured to circumscribe a cut area and defines a cutting edge that extends beyond the frame in a cutting direction. A plurality of fenestration blades are oriented to extend across the cut area circumscribed by the perimeter blade. A plurality of cutouts are formed in a cutting edge of at least a plurality of, and preferably each of, the plurality of fenestration blades.

A further aspect of the application discloses a fenestrated tissue graft press cutting die assembly that includes a first edge blade and a second edge blade that each include a continuous cutting edge configured to sever a material, being cut. A plurality of field blades are disposed between the first edge blade and the second edge blade. Each field blade has a discontinuous cutting edge formed along at least a portion of a longitudinal edge of the respective field blade such that the field blades perforate an area of the material being cut which is circumscribed by the continuous cutting edge.

Yet another aspect of the application discloses a method of forming a press cutting die assembly. The method includes providing a perimeter blade assembly that is configured to circumscribe a cut area. A plurality of fenestration blades are provided that extend between the perimeter blade assembly. Each of the fenestration blades includes a discontinuous cutting edge that generates a generally uniform perforation pattern within the cut area bounded by the perimeter blade.

It is appreciated that the aspects and features of the application summarized above are not limited to any one particular embodiment of the invention. That is, many or all of the aspects above may be achieved with any particular embodiment of the invention. Those skilled in the art will appreciate that the invention may be embodied in a manner preferential to one aspect or group of aspects and advantages as taught herein. These and various other aspects, features, and advantages of the, present invention will be made apparent from the following detailed description and the drawings.

BRIEF DESCRIPTION OF THE DRAWINGS

The drawings illustrate a preferred embodiment presently contemplated for carrying out the invention. In the drawings.

DETAILED DESCRIPTION OF THE PREFERRED EMBODIMENT

Figure 1:
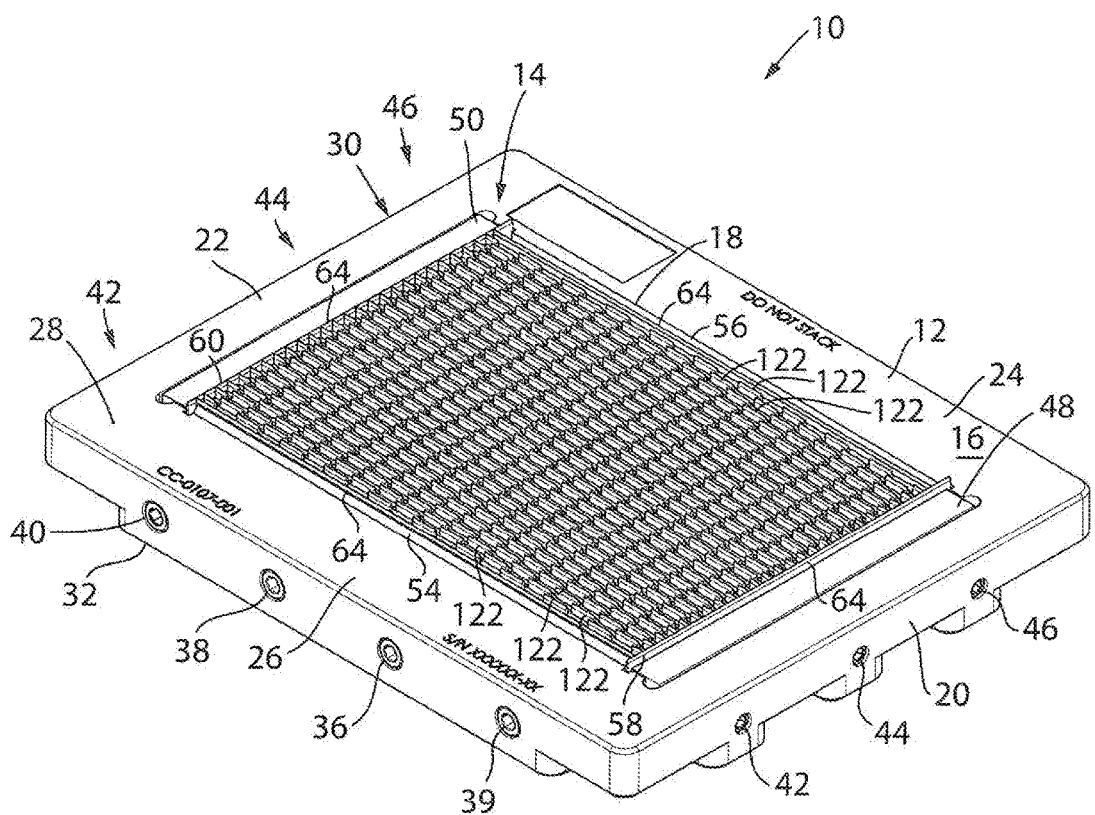
FIG. 1 is an cutting side perspective view of a press cutting die assembly according to the present invention.
Figure 2:
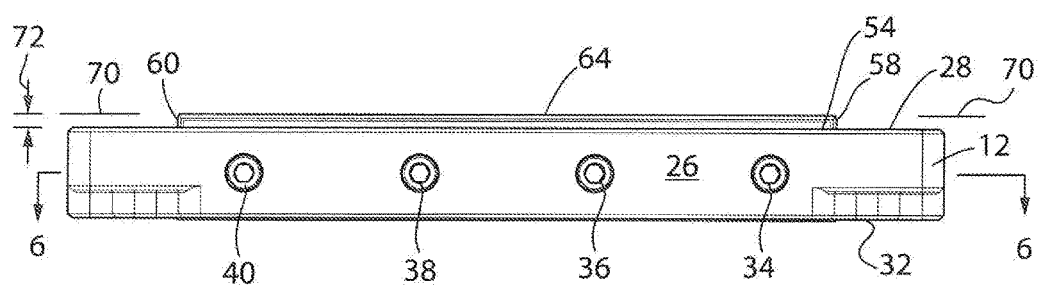
FIG. 2 is an edge side elevation view of the press cutting die assembly shown in FIG. 1.
Figure 3:
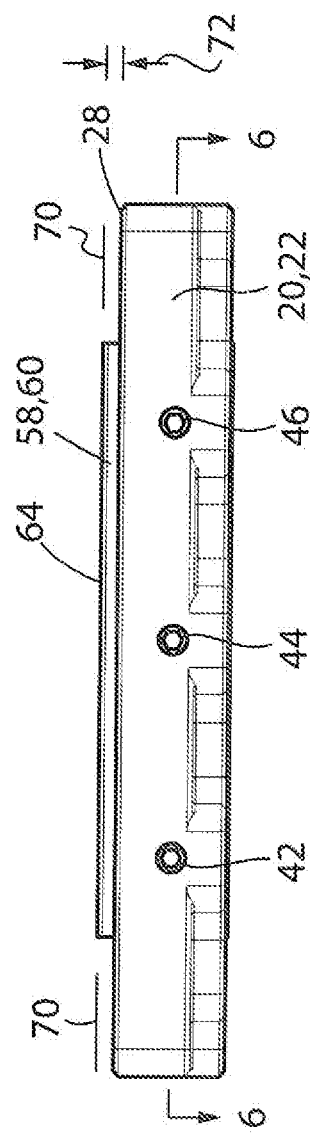
FIG. 3 is an end side elevation view of the press cutting die assembly shown in FIG. 1.

FIG. 1 shows a press cutting die assembly 10 according to the present invention. Referring to FIGS. 1-3, die assembly 10 includes a base or frame 12 that is constructed to support a blade assembly 14 relative thereto. Frame 12 is defined by a body 16 that defines a cavity, recess, or blade window 18 associated with supporting blade assembly 14 relative thereto. Body 16 includes end portions 20, 22 and edge portions 24, 26 that are continuous or constructed to cooperate with one another to generally surround blade window 18.

A first side 28 of frame 12 is associated with a cutting side 30 of die assembly 10 and blade assembly 14. As commonly understood, the cutting side 30 of die assembly 10 is associated with the lateral side of die assembly 10 that is constructed to be introduced to a cutting material and effectuate the cutting operation as a cutting edge side of blade assembly 14 is passed therethrough. An opposing side 32 of frame 12 faces in a generally opposite lateral direction. As disclosed further below with respect to FIG. 4, cutting die assembly 10 includes one or more fasteners 34, 36, 38, 40 that cooperate with edge portions 24, 26 of frame 12 and pass through blade window 18 and cooperate with blade assembly 14 positioned therein.

One or more adjusters 42, 44, 46 cooperate with respective end portions 20, 22 of frame 12 and cooperate with a spacer or crowder 48, 50 disposed proximate the respective end portion 20, 22 of frame 12. As explained further below with respect, to FIGS. 4-6, fasteners 34, 36, 38, 40; adjusters 42, 44, 46; and crowders 48, 50 cooperate with frame 12 and blade assembly 14 to maintain a generally orthogonal and contacting or compressing orientation of respective portions of blade assembly 14 relative to one another and frame 12 as described further below.

Still referring to FIGS. 1-3, blade assembly 14 includes a pair of edge blades 54, 56 that extend along the generally opposite longitudinal edges of blade assembly 14 and a pair of end blades 58, 60 that extend along the generally opposite lateral edges or ends of blade assembly 14. Each of edge blades 54, 56 and end blades 58, 60 include a cutting edge 64 defined by the respective blade 54, 56, 58, 60. Although shown as discrete edge and end blade portions, it is appreciated that the edge and end blade portions could be formed by a generally continuous blade member wherein discrete sections of the blade member are bent relative to one another so as to extend in generally crossing directions relative to one another. Regardless of the formation methodology employed, the cutting edges 64 defined by blades 54, 56, 58, 60 circumscribe an area to be cut from a graft material is described further below with respect to FIG. 7. As shown in FIGS. 2 and 3, a plane, indicated by line 70, is defined by cutting edge 64 and is oriented to be offset, as indicated by dimension arrows 72, from the surface associated with cutting side 28 of frame 12. Such a consideration allows blades 54, 56, 58, 60 to be pressed through a material to be cut without interference and/or contact of frame 12 with the cut material.

Figure 4:
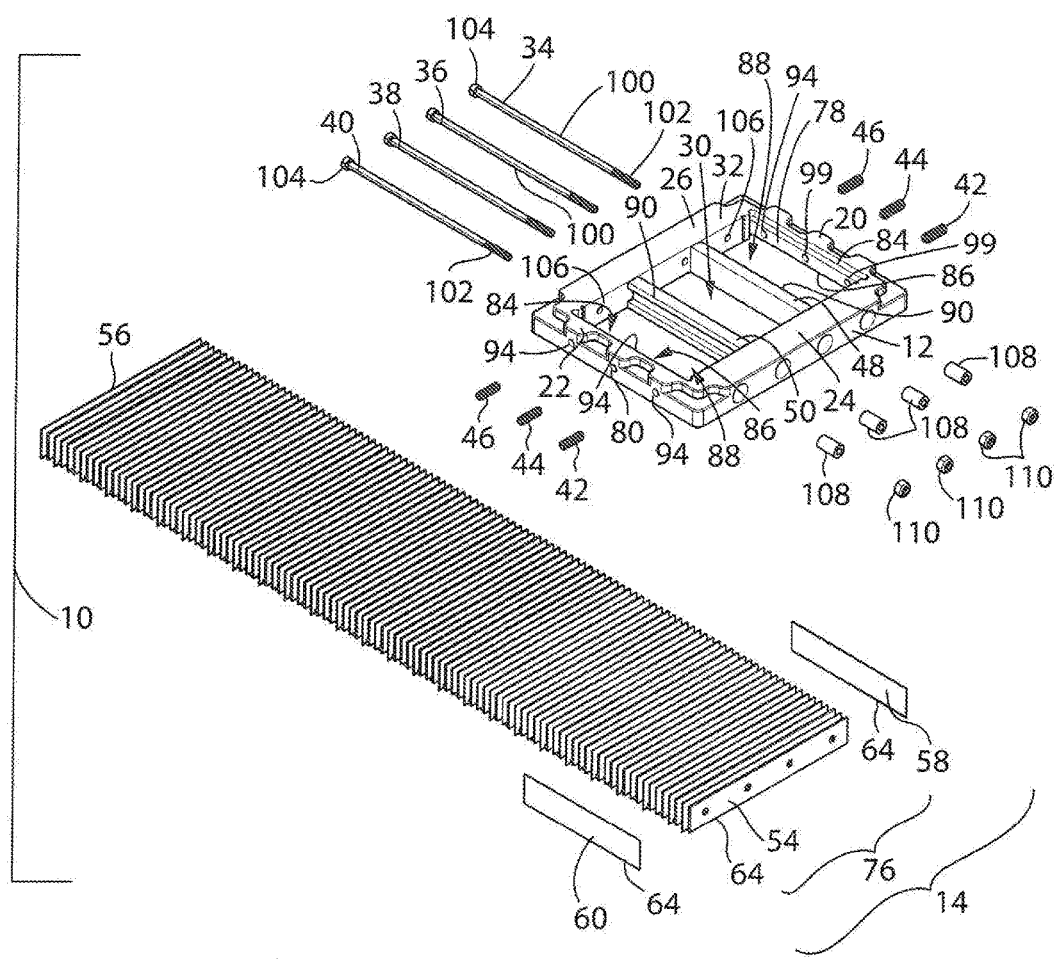
FIG. 4 is an exploded perspective view of the press cutting die assembly shown in FIG. 1.

Referring to FIG. 4, press die assembly 10 includes a blade stack 76 that is constructed to be disposed between end blades 58, 60. It should be appreciated that the orientation of press die assembly 10 shown in FIG. 4 is from the opposite or non-cutting side 32 of frame 12 of assembly 10 as compared to the cutting side shown in FIG. 1. It should be further appreciated that blade stack 76 has been expanded merely for illustration purposes. When assembled, the respective components of blade stack 76, as described further below with respect to FIG. 5, are configured to be oriented in adjacent or touching proximity relative to one another and such that blade stack 76 can be oriented substantially between end blades 58, 60 with the respective longitudinal ends of each discrete portion of the blade stack 76 in close if not touching proximity relative to the adjacent respective end blade 58, 60.

Still referring to FIG. 4, an interior of blade window 18 facing surface 78, 80 of portions 20, 22 of frame 12 includes opposing channels 84, 86 that are shaped to generally match a contour 88 associated with a frame facing side 90 of an adjacent spacer or crowder 48, 50. When fully assembled, crowders 48, 50 are oriented in close or overlapping proximity to the respective portions 20, 22 of frame 12. Adjusters 42, 44, 46 cooperate with respective threaded cavities 94 defined by frame 12. Adjusters 42, 44, 46 cooperate with respective threaded cavities 94 such that crowders 48, 50 can be oriented in a generally orthogonal or perpendicular orientation relative to edge portions 24, 26 defined by frame 12 and the blade stack 76 associated therewith. Crowders 48, 50 further effectuate a desired longitudinal alignment between each of edge blades 54, 56 and the respective components of blade stack 76 as disclosed further below.

Each of fasteners 34, 36, 38, 40 includes an elongated body 100 having a threaded portion 102 disposed at one end thereof and a head portion 104 associated with the opposite end thereof. Elongated body 100 of each fastener is constructed to slidably cooperate with a respective opening 106 associated with frame 12, traverse blade window 18, slidably cooperate with a respective sleeve 108, and engage a nut 110 via threaded portion 102. Fasteners 34, 36, 38, 40; respective sleeves 108; respective nuts 110; and frame 12 are constructed to allow fasteners to maintain a contact engagement between the adjacent structures associated with blade stack 76 when die assembly 10 is assembled as disclosed further below with respect to FIG. 6.

Figure 5:
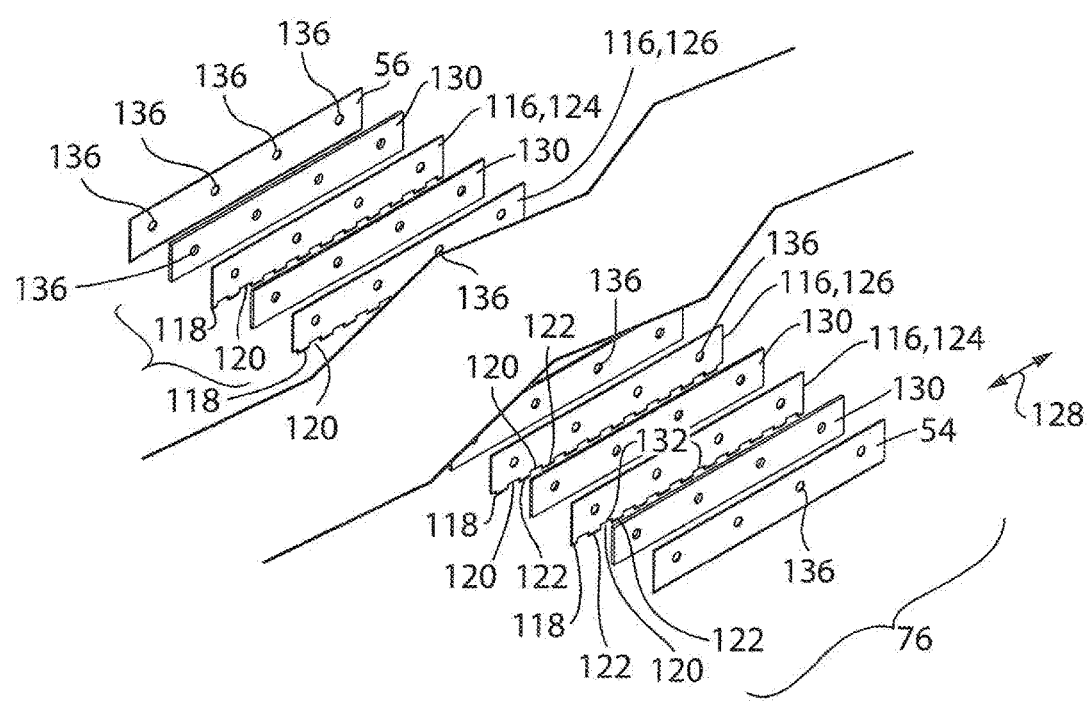
FIG. 5 is a perspective view of a portion of a blade stack of the press cutting die assembly shown in FIG. 1.

As shown in FIG. 5, blade stack 76 includes edge blades 54, 56 that are disposed along the opposite longitudinal edges thereof. Between edge blades 54, 56, blade stack 76 includes a plurality of perforation, field, or fenestration blades 116. Each fenestration blade 116 defines a discontinuous cutting edge 118 that extends along the longitudinal edges thereof. The discontinuous cutting edge 118 associated with each fenestration blade 116 includes a gap or cutout 120 that is disposed between adjacent cutting portions 122 along the longitudinal length of the respective discontinuous cutting edge 118. When assembled, cutting portions 122 of each cutting edge 118 associated with each fenestration blade lies in plane 70 associated with the continuous cutting edge defined by edge and end blades 54, 56, 58, 60.

In a preferred embodiment, the length associated with each discrete cutting portion 122 and discrete cutout 120 of each fenestration blade 116 extend a generally similar distance relative to one another along the respective fenestration blade 116. It is appreciated that the geometry associated the cutting portions 122 and cutouts 120 associated with fenestration blades 116 could be provided in various geometries. Fenestration blades 116 are further segregated into a first group or set of blades 124 and a second group or set of blades 126. Referring to FIGS. 1 and 5 and comparing the respective cutting edge 118 of a first group fenestration blade 124 relative to the cutting edge 118 of a second group fenestration blade 126, it should be appreciated that the cutting portion 122 of a first group fenestration blade 124 is generally aligned with a cutout 120 associated with a second group fenestration blade 126 when considered in the stacked direction. It should further be appreciated that the cutting portions 122 and cutouts 120 of the first group of fenestration blades 124 are aligned with one another in the stack direction and the cutting portion 122 and the cutouts 120 of the second group of fenestration blades 126 are aligned with one another in the stack direction. Although the discrete cutting portions and cutouts associated with the discrete groups of fenestration blades are aligned with the other blades in the same group in the stack direction, discrete cutting portions 122 and cutouts 120 associated with the first group fenestration blades 124 are offset in the longitudinal directions, indicated by arrow 128, relative to the respective to the discrete cutting portions 122 and cutouts 120 associated with each second group fenestration blade 126. Such a consideration produces a repeating and substantially uniform staggered pattern of each discrete fenestration within the boundary of the edge and end blades 54. 56, 58, 60 of die assembly 10.

Still referring to FIG. 5, a spacer 130 is disposed between adjacent fenestration blades 116 as well as respective edge blades 54, 56 and an adjacent fenestration blade 116. Preferably, each spacer 130 is provided to have a uniform thickness in the stack direction and a depth such that no portion of a respective spacer 130 extends beyond a bottom 132 associated with each discrete cutout 120 of an adjacent fenestration blade 116. Each of edge blades 54, 56, fenestration blades 116, and spacers 130 associated with blade stack 76 includes a plurality of openings 136 configured to accommodate the slidable passage of the elongate body 100 of a respective fasteners 34, 36, 38, 40 therethrough as disclosed further below with respect to FIG. 6. As mentioned above, when fully assembled, the cutting portions 122 of each fenestration blade 116 is oriented to lie in plane 70 associated with the cutting edge 64 of edge blades 54, 56 and end blades 58, 60. Such considerations ensure that the cutting portion 122 associated with each fenestration blade 116 forms a cut, hole, or perforation in the graft tissue and that all but those perforations formed by the cutting portions 122 of the fenestration blades that lie adjacent the end blades 58, 60 are circumferentially bounded by the graft tissue. Such a consideration ensures generally uniform propagation of the fenestration pattern across the entirety of the graft blank as disclosed further below with respect to FIGS. 7 and 8.

Figure 6:
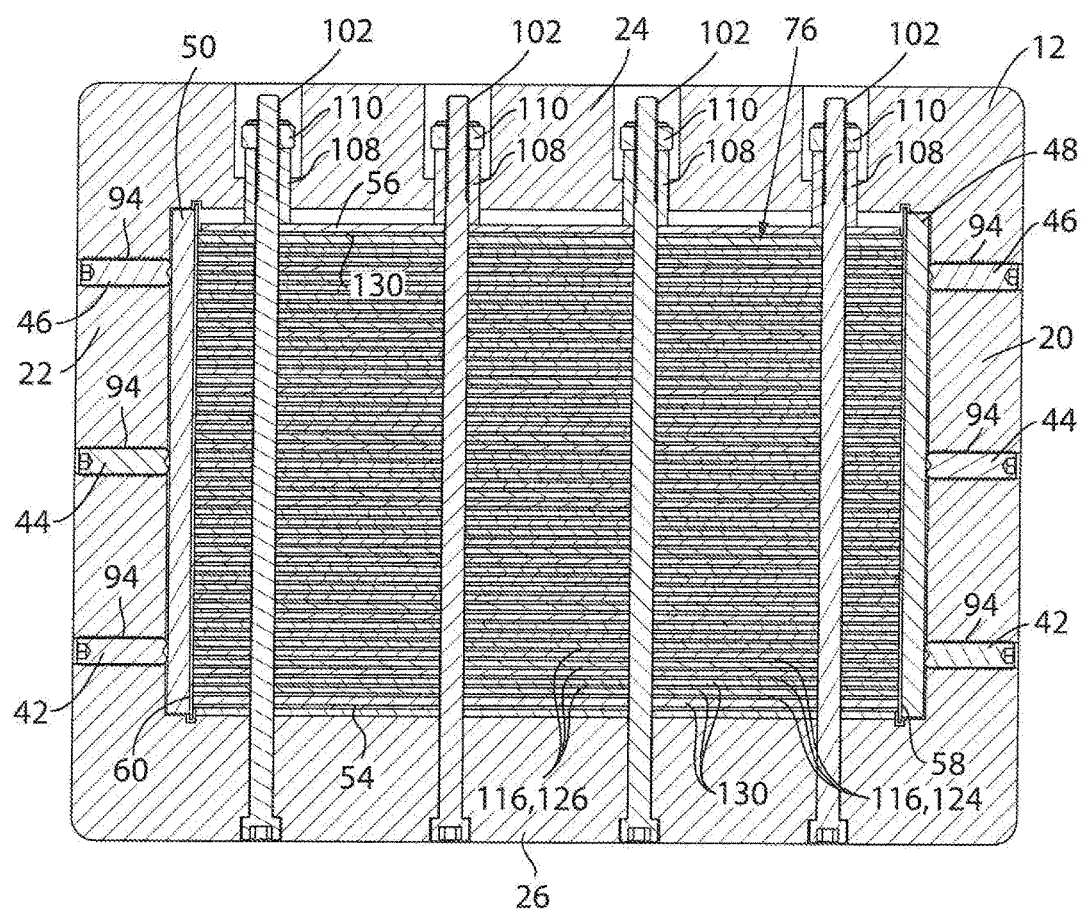
FIG. 6 is a cross section view of the, press cutting die assembly shown in FIG. 1 taken along line 6-6 shown in FIGS. 2 and 3.

As shown in FIG. 6, when assembled, blade stack 76 is bounded or circumscribed by edge blades 54, 56 and end blades 58, 60. Fenestration blades 116 extend in a longitudinal direction between end blades 58, 60. When considered in the stack direction, fenestration blades 116 are oriented in a generally repeating pattern inboard of a respective edge blade 54, 56 wherein the pattern propagates in a pattern of a respective spacer 130, a respective one of first or second group fenestration blades 124, 126, another spacer 130, and a respective one of the other of first or second group fenestration blades 124, 126. Such a pattern repeats in the lateral or stack direction relative to blade stack 76 to the opposing edge blade 56 and the respective spacer 130 that is disposed adjacent to the opposing edge blade 56. Although disclosed as repeating in a pattern associated with two respective first and second group of fenestration blades 124, 126 as designated by their respective cutting edges, it is appreciated that the fenestrations could be provided in virtually any pattern via manipulation of the number of sets of fenestration blade groups and/or the pattern associated with the cutouts 120 and cutting edges 122 associated therewith.

Figure 7:
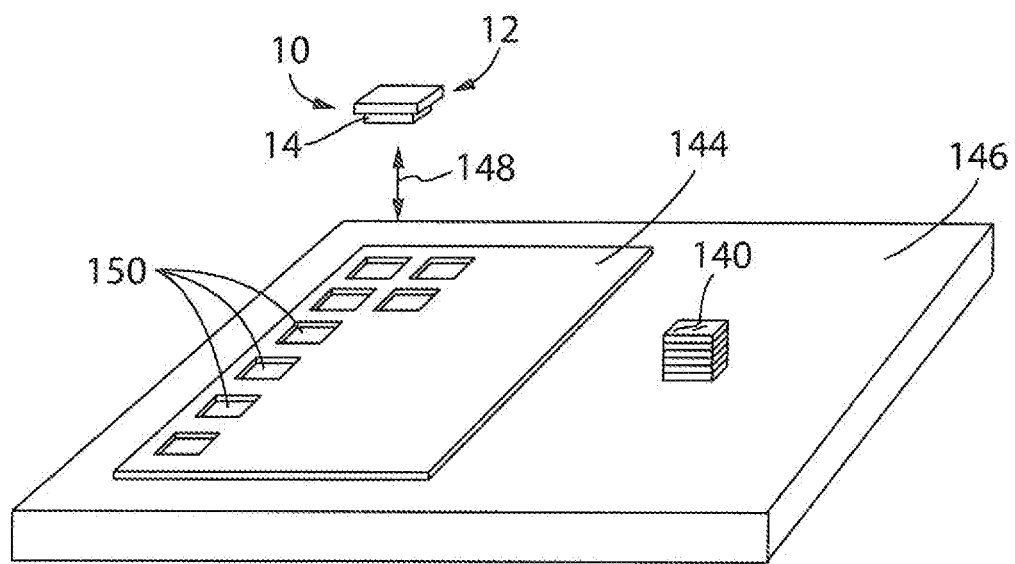
FIG. 7 is a perspective view of a graphical representation of the press cutting die assembly shown in FIG. 1 associated with a section of graft tissue.
Figure 8:
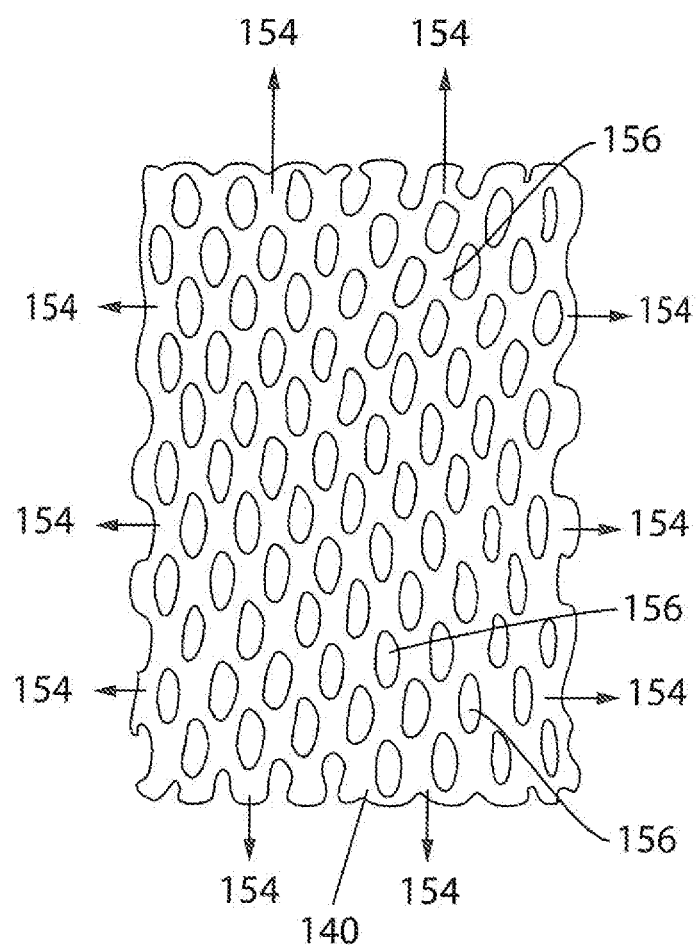
FIG. 8 is a top plan view of a portion of a press cut graft tissue blank formed by the press cutting die shown in FIG. 1 when subjected to radially outward directed tension forces.

Referring to FIGS. 7 and 8, die assembly 10 is constructed to cut and fenestrate a graft tissue blank 140 each time blade assembly 14 is pressed into a bulk graft material sheet 144. FIG. 7 shows an exemplary press cutting process associated with use of die assembly 10. As shown in FIG. 7, during press cutting operations, a blank material, such as a grail material 144, is associated with a platen or other support structure 146. Each introduction of blade assembly 14 of die assembly 10 to the graft material 144, and downward translation of the same, indicated by arrow 148, cuts and fenestrates a respective graft or graft blank 140 from the sheet material 144 and leaves a cutout 150 associated with each graft blank 140 that is removed from material 144. It should be appreciated that the shape of die assembly 10, and particularly the cutting edge associated therewith, will commonly dictate the most efficient consumption or usage of the blank material 144 to generate the desired fenestrated graft blanks 140 therefrom. Although suitable for cutting fenestrated grafts 140, it is further appreciated that die assembly 10 can be utilized to cut various other materials such as bandages, human or other animal organs, as well as other materials used in medical environments such as wet bandages, wet gauzes, placentas, etc. where fenestration of the underlying material is desired.

It is appreciated that fenestrated grafts 140 can be removed manually from die assembly 10 or extracted in other manners, such as via a blower or vacuum extraction, tea remove the cut and fenestrated grafts 140 from die assembly 10. Preferably, each of end and edge blades 54, 56, 58, 60 and fenestration blades 116 are oriented orthogonally parallel or perpendicular to frame 12 and the respective cutting edges associated with each of the perimeter and fenestration or field blades is preferably maintained in a plane that is parallel to frame 12 such that each graft cutting operation results in a circumferential severing of the fenestrated graft 140 cut from bulk material 144. Such a consideration reduces the potential that a supplemental cut operation will be required to effectuate fall separation between the respective grafts from the bulk graft material.

Die assembly 10 and the plurality of perimeter and field or fenestration blades associated therewith provide a press cutting die assembly that can be economically produced, is robust, does not adversely affect the sanitation of the materials to which it is applied, and produces fenestrated graft blanks that are ready for use without supplemental fenestration. As shown in FIG. 8, when subjected to radially outward directed tension forces in the plane associated with the fenestrated graft blanks 140, as indicted by arrows 154, the uniformity of the formation of the fenestrations allows each graft to be stretched without failure of the boundary associated with any discrete fenestration opening 156 thereby improving healing associated with the same. It has been shown that fenestrated graft blanks produced with die assembly 10 can be stretched 3-4 times per unit of donor tissue. Die assembly 10 is sufficiently robust to tolerate subsequent sanitation and disinfectant processes and economically producible so as to tolerate periodic disposable and replacement of the die assembly. Die assembly 10 further mitigates the shortcomings of current graft fenestration processes as disclosed above.

Therefore, one embodiment of the invention includes a press cutting die assembly that includes a frame that is configured to support a blade stack. The blade stack includes a perimeter blade assembly that is configured to circumscribe a cut area and defines a cutting edge that extends beyond the frame in a cutting direction. A plurality of fenestration blades are oriented to extend across the cut area circumscribed by the perimeter blade. A plurality of cutouts are formed in a cutting edge of at least a plurality of, and preferably each of, the plurality of fenestration blades portions.

A further embodiment of the invention that is useable or combinable with one or more of the features or aspects of the other embodiments of the invention includes a fenestrated tissue graft press cutting die assembly. The press cutting die assembly includes a first edge blade and a second edge blade that each include a continuous cutting edge that is configured to sever a material being cut. A plurality of field blades are disposed between the first edge blade and the second edge blade. Each field blade has a discontinuous cutting edge formed along at least a portion of longitudinal edge of the respective field blade such that the field blades perforate an area of the material being cut that is circumscribed by the continuous cutting edge.

Yet another embodiment of the invention that is combinable or usable with one or more of the features or aspects of the above embodiments includes a method of forming a press cutting die assembly. The method includes providing a perimeter blade assembly that is configured to circumscribe a cut area. A plurality of fenestration blades are provided that extend between the perimeter blade assembly. Each of the fenestration blades includes a discontinuous cutting edge that generates a generally uniform perforation pattern within the cut area bounded by the perimeter blade.

The present invention has been described in terms of the preferred embodiments, and it is recognized that equivalents, alternatives, and modifications, aside from those expressly stated, are possible and within the scope of the appending claims. It is further appreciated that the respective features of any one of the embodiments discussed above is not necessarily solely exclusive thereto.

What is claimed is:

1. A press cutting die assembly, the assembly comprising: a frame configured to support a blade stack; and the blade stack comprising:
    a perimeter blade configured to circumscribe a cut area and having a cutting edge that extends beyond the frame in a cutting direction;
    a plurality of fenestration blades oriented to extend across the cut area circumscribed by the perimeter blade; and
    a plurality of cutouts formed in a cutting edge of a plurality of the plurality of fenestration blades portions.

2. The assembly of claim 1 wherein the plurality of fenestration blades include a first set of fenestration blades and a second set of fenestration blades and the plurality of cutouts associated with the cutting edge of the first set of fenestration blades is offset from the plurality of cutouts associated with the cutting edge of the second set of fenestration blades relative to adjacent respective fenestration blades.

3. The assembly of claim 1 further comprising a spacer disposed between adjacent blades of the plurality of fenestration blades.

4. The assembly of claim 1 further comprising an end plate supported by the frame and disposed at an end of the blade stack.

5. The assembly of claim 4 further comprising another end plate supported by the frame and disposed at an opposite end of the blade stack.

6. The assembly of claim 5 wherein at least one of the end plate and another end plate are adjustable relative to the frame.

7. The assembly of claim 1 further comprising at least one fastener that passes through the blade stack in a lateral direction and traverses the cut area such that opposing ends of the at least one fastener cooperate with the frame.

8. The assembly of claim 7 further comprising a plurality of fasteners that pass through the blade stack in the lateral direction wherein opposing ends of each fastener cooperate with the frame.

9. A fenestrated tissue graft press cutting die assembly, the assembly comprising:
   a first edge blade and a second edge blade that each include a continuous cutting edge configured to sever a material being cut; and
   a plurality of field blades disposed between the first edge blade and the second edge blade, each field blade having a discontinuous cutting edge formed along at least a portion of longitudinal edge of the respective field blade such that each field blade perforate an area of the material being cut circumscribed by the continuous cutting edge.

10. The assembly of claim 9 further comprising a frame configured to support the first edge blade, the second edge blade, and the plurality of field blades relative to one another.

11. The assembly of claim 10 further comprising at least one fastener that passes through the plurality of field blades at a location offset from the discontinuous cutting edge.

12. The assembly of claim 10 further comprising an end plate disposed between the frame and a respective longitudinal end of the each of the first edge blade, the second edge blade, and the plurality of field blades.

13. The assembly of claim 12 further comprising another end plate associated with an opposite respective longitudinal end of each of the first edge blade, the second edge blade, and the plurality of field blades.

14. The assembly of claim 13 further comprising at least one adjuster engaged with the frame and a respective one of the end plate and the another end plate.

15. The assembly of claim 9 wherein the plurality of field blades include a first group of field blades and a second group of field blades wherein the discontinuous cutting edge of each of the first group of field blades are aligned with one another and are staggered relative to the discontinuous cutting edge of each of the second group of field blades.

16. The assembly of claim 9 further comprising a spacer disposed between adjacent blades of the plurality of field blades.

17. The assembly of claim 9 further comprising a first end blade and a second end blade that are each oriented at crossing directions relative to the first edge blade and the second edge blade and each include a continuous cutting edge disposed in a common plane with the continuous cutting edge defined by the first edge blade and the second edge blade.

18. A method, of forming a press cutting die assembly, the method comprising:
   providing a perimeter blade assembly configured to circumscribe a cut area; and
   providing a plurality of fenestration blades that extend between the perimeter blade assembly and each include a discontinuous cutting edge that generates a perforation pattern within the cut area bounded by the perimeter blade.

19. The method of claim 18 further comprising a frame configured to maintain an orientation of the perimeter blade assembly and the plurality of fenestration blades relative to one another.

20. The method of claim 18 further comprising orienting the plurality of fenestration blades so that the perforation pattern is provided in at least two repeating patterns of perforations.

* * * * *